United States Patent
Banet et al.

(10) Patent No.: US 7,658,716 B2
(45) Date of Patent: Feb. 9, 2010

(54) VITAL SIGNS MONITOR USING AN OPTICAL EAR-BASED MODULE

(75) Inventors: Matthew John Banet, Del Mar, CA (US); Brett George Morris, San Diego, CA (US); Henk Visser, San Diego, CA (US)

(73) Assignee: Triage Wireless, Inc., San Diego, CA (US)

( * ) Notice: Subject to any disclaimer, the term of this patent is extended or adjusted under 35 U.S.C. 154(b) by 0 days.

(21) Appl. No.: 10/904,971

(22) Filed: Dec. 7, 2004

(65) Prior Publication Data

US 2006/0122517 A1 Jun. 8, 2006

(51) Int. Cl.
*A61B 5/00* (2006.01)
(52) U.S. Cl. ...................................... 600/485; 600/500
(58) Field of Classification Search ......... 600/485–503, 600/480
See application file for complete search history.

(56) References Cited

U.S. PATENT DOCUMENTS

| | | | |
|---|---|---|---|
| 3,412,729 A | 11/1968 | Smith | |
| 4,063,551 A | 12/1977 | Sweeny | |
| 4,080,966 A | 3/1978 | McNally et al. | |
| 4,320,767 A | 3/1982 | Villa-Real | |
| 4,367,752 A | 1/1983 | Jimenez et al. | |
| 4,380,240 A | 4/1983 | Jobsis et al. | |
| 4,425,920 A | 1/1984 | Bourland et al. | |
| 4,681,118 A | 7/1987 | Asai et al. | |
| 4,777,954 A | 10/1988 | Keusch et al. | |
| 4,825,879 A | 5/1989 | Tan et al. | |
| 4,846,189 A * | 7/1989 | Sun | 600/492 |
| 4,869,261 A | 9/1989 | Penaz | |
| 4,917,108 A | 4/1990 | Mault | |
| 5,002,055 A | 3/1991 | Merki et al. | |
| 5,038,792 A | 8/1991 | Mault | |
| 5,111,817 A | 5/1992 | Clark et al. | |
| 5,140,990 A | 8/1992 | Jones et al. | |
| 5,178,155 A | 1/1993 | Mault | |
| 5,179,958 A | 1/1993 | Mault | |
| 5,213,099 A * | 5/1993 | Tripp, Jr. | 600/324 |
| 5,237,997 A | 8/1993 | Greubel et al. | |
| 5,309,916 A | 5/1994 | Hatschek | |
| 5,368,039 A | 11/1994 | Moses | |
| 5,435,315 A | 7/1995 | McPhee et al. | |

(Continued)

OTHER PUBLICATIONS

Yang, Boo-Ho et al., Cuff-Less Continious Monitoring of Beat-To-Beat Pressure Using Sensor Fusion, submitted to IEEE Transactions on Biomedical Engineering.

Weijia Cui, Lee E. et al., In Vivo Reflectance of Blood and Tissue as a Function of Light Wavelength, submitted to IEEE Transactions on Biomedical Engineering, vol. 37 No. 6.

*Primary Examiner*—Robert L Nasser
(74) *Attorney, Agent, or Firm*—Wilmer Cutler Pickering Hale & Dorr LLP

(57) ABSTRACT

The invention provides a system for measuring blood pressure from a patient that includes: 1) an optical module configured to be worn on the patient's ear and comprising at least one optical source and a photodetector; 2) a calibration source configured to make a blood pressure measurement; and, 3) a processing module configured to: i) receive a first signal from the optical module; ii) receive a second signal from the calibration source; iii) process the first and second signals to generate a calibration table; and iv) receive a third signal from the optical module and compare it to the calibration table to determine the patient's blood pressure.

22 Claims, 3 Drawing Sheets

U.S. PATENT DOCUMENTS

| | | | |
|---|---|---|---|
| 5,485,848 A | 1/1996 | Jackson et al. | |
| 5,551,438 A | 9/1996 | Moses | |
| 5,632,272 A | 5/1997 | Diab et al. | |
| 5,671,750 A * | 9/1997 | Shinoda | 600/495 |
| 5,727,558 A | 3/1998 | Hakki et al. | |
| 5,743,857 A * | 4/1998 | Shinoda et al. | 600/496 |
| 5,836,300 A | 11/1998 | Mault | |
| 5,857,975 A | 1/1999 | Golub | |
| 5,865,755 A | 2/1999 | Golub | |
| 5,865,758 A | 2/1999 | Louzianine | |
| 5,891,042 A | 4/1999 | Sham et al. | |
| 5,921,936 A | 7/1999 | Inukai et al. | |
| 6,004,274 A * | 12/1999 | Nolan et al. | 600/486 |
| 6,013,009 A | 1/2000 | Karkanen | |
| 6,050,940 A | 4/2000 | Braun et al. | |
| 6,176,831 B1 | 1/2001 | Voss et al. | |
| 6,224,548 B1 | 5/2001 | Gopinathan et al. | |
| 6,245,014 B1 | 6/2001 | Brainard, II | |
| 6,272,936 B1 | 8/2001 | Oreper | |
| 6,280,390 B1 * | 8/2001 | Akselrod et al. | 600/485 |
| 6,334,065 B1 | 12/2001 | Al-Ali et al. | |
| 6,336,900 B1 | 1/2002 | Alleckson et al. | |
| 6,364,842 B1 | 4/2002 | Amano et al. | |
| 6,371,921 B1 | 4/2002 | Caro et al. | |
| 6,375,614 B1 | 4/2002 | Braun et al. | |
| 6,398,727 B1 | 6/2002 | Bui et al. | |
| 6,413,223 B1 | 7/2002 | Yang et al. | |
| 6,432,061 B1 | 8/2002 | Nissila et al. | |
| 6,443,905 B1 | 9/2002 | Nissila et al. | |
| 6,443,906 B1 | 9/2002 | Ting et al. | |
| 6,475,146 B1 | 11/2002 | Frelburger et al. | |
| 6,475,153 B1 | 11/2002 | Khair et al. | |
| 6,477,397 B1 | 11/2002 | Ronkainen et al. | |
| 6,511,436 B1 | 1/2003 | Asmar | |
| 6,514,211 B1 | 2/2003 | Baura | |
| 6,527,711 B1 | 3/2003 | Stivoric et al. | |
| 6,533,729 B1 | 3/2003 | Khair et al. | |
| 6,546,269 B1 | 4/2003 | Kurnik | |
| 6,553,247 B1 | 4/2003 | Rytky | |
| 6,556,852 B1 | 4/2003 | Schulze et al. | |
| 6,558,321 B1 | 5/2003 | Burd et al. | |
| 6,571,200 B1 | 5/2003 | Mault | |
| 6,595,929 B2 | 7/2003 | Stivoric et al. | |
| 6,599,251 B2 | 7/2003 | Chen et al. | |
| 6,605,038 B1 | 8/2003 | Teller et al. | |
| 6,605,044 B2 | 8/2003 | Bimbaum | |
| 6,609,023 B1 | 8/2003 | Fischell et al. | |
| 6,612,984 B1 | 9/2003 | Kerr, II | |
| 6,616,613 B1 * | 9/2003 | Goodman | 600/504 |
| 6,645,154 B2 | 11/2003 | Oka | |
| 6,645,155 B2 | 11/2003 | Inukai et al. | |
| 6,652,466 B2 | 11/2003 | Sugo et al. | |
| 6,678,543 B2 | 1/2004 | Diab et al. | |
| 6,681,454 B2 | 1/2004 | Modgil et al. | |
| 6,714,804 B2 | 3/2004 | Al-Ali et al. | |
| 6,723,054 B1 | 4/2004 | Baruch et al. | |
| 6,733,447 B2 | 5/2004 | Lai et al. | |
| 6,740,045 B2 | 5/2004 | Amano | |
| 6,775,566 B2 | 8/2004 | Nissila et al. | |
| 6,808,473 B2 | 10/2004 | Hisano et al. | |
| 6,813,511 B2 | 11/2004 | Diab et al. | |
| 6,814,705 B2 | 11/2004 | Kawaguchi | |
| 6,852,083 B2 * | 2/2005 | Caro et al. | 600/485 |
| 6,871,084 B1 | 3/2005 | Kingsley et al. | |
| 6,918,879 B2 * | 7/2005 | Ting et al. | 600/485 |
| 2002/0183627 A1 | 12/2002 | Nishii et al. | |
| 2004/0030261 A1 * | 2/2004 | Rantala | 600/561 |
| 2004/0260186 A1 * | 12/2004 | Dekker | 600/483 |
| 2005/0228299 A1 * | 10/2005 | Banet | 600/485 |

* cited by examiner

VITAL SIGNS MONITOR USING AN OPTICAL EAR-BASED MODULE

CROSS REFERENCES TO RELATED APPLICATION

Not Applicable

BACKGROUND OF THE INVENTION

The present invention relates to medical devices for monitoring vital signs such as heart rate, pulse oximetry, and blood pressure.

DESCRIPTION OF THE RELATED ART

Pulse oximeters are medical devices featuring an optical module, typically worn on a patient's finger or ear lobe, and a processing module that analyzes data generated by the optical module. The optical module typically includes first and second light sources (e.g., light-emitting diodes, or LEDs) that transmit optical radiation at, respectively, red ($\lambda\sim 630$-$670$ nm) and infrared ($\lambda\sim 800$-$1200$ nm) wavelengths. The optical module also features a photodetector that detects radiation transmitted or reflected by an underlying artery. Typically the red and infrared LEDs sequentially emit radiation that is partially absorbed by blood flowing in the artery. The photodetector is synchronized with the LEDs to detect transmitted or reflected radiation. In response, the photodetector generates a separate radiation-induced signal for each wavelength. The signal, called a plethysmograph, varies in a time-dependent manner as each heartbeat varies the volume of arterial blood and hence the amount of transmitted or reflected radiation. A microprocessor in the pulse oximeter processes the relative absorption of red and infrared radiation to determine the oxygen saturation in the patient's blood. A number between 94%-100% is considered normal, while a value below 85% typically indicates the patient requires hospitalization. In addition, the microprocessor analyzes time-dependent features in the plethysmograph to determine the patient's heart rate.

Pulse oximeters work best when the appendage they attach to (e.g., a finger) is at rest. If the finger is moving, for example, the light source and photodetector within the optical module typically move relative to the hand. This generates 'noise' in the plethysmograph, which in turn can lead to motion-related artifacts in data describing pulse oximetry and heart rate. Ultimately this reduces the accuracy of the measurement.

Various methods have been disclosed for using pulse oximeters to obtain arterial blood pressure values for a patient. One such method is disclosed in U.S. Pat. No. 5,140,990 to Jones et al., for a 'Method Of Measuring Blood Pressure With a Photoplethysmograph'. The '990 patent discloses using a pulse oximeter with a calibrated auxiliary blood pressure to generate a constant that is specific to a patient's blood pressure. Another method for using a pulse oximeter to measure blood pressure is disclosed in U.S. Pat. No. 6,616,613 to Goodman for a 'Physiological Signal Monitoring System'. The '613 patent discloses processing a pulse oximetry signal in combination with information from a calibrating device to determine a patient's blood pressure.

BRIEF SUMMARY OF THE INVENTION

An object of the invention is to provide a cuffless monitor that makes a continuous optical measurement from a patient's ear or forehead to determine real-time blood pressure, pulse oximetry, and heart rate. In one aspect, the invention provides a system for measuring blood pressure from a patient that features: 1) an optical module configured to be worn on (or in) the patient's ear or forehead that includes at least one optical source and a photodetector; 2) a calibration source configured to make a blood pressure measurement; and, 3) a processing module configured to: i) receive a first signal from the optical module; ii) receive a second signal from the calibration source; iii) process the first and second signals to generate a calibration table; and iv) receive a third signal from the optical module and compare it to the calibration table to determine the patient's blood pressure.

In another aspect, the invention provides a system for measuring blood pressure from a patient that features: 1) an optical module comprising at least one optical source and a photodetector; 2) a calibration source configured to make a blood pressure measurement; 3) a processing module configured to receive a first signal from the optical module and a second signal from the calibration source, and in response calculate a blood pressure value; and 4) a wireless transmitter configured to receive blood pressure values from both the calibration source and processing module and to transmit the blood pressure values over a wireless network.

In embodiments, an ear-worn clip includes the optical module (e.g., a photodetector and first and second LEDs that emit, respectively, red radiation and infrared radiation). The calibration source is typically a cuff-based blood pressure module that includes a cuff and a pump worn around the patient's arm. In other embodiments, the optical module includes a short-range wireless transmitter configured to send signals to the processing module, which in turn may include a matched short-range wireless receiver.

The short-range wireless transceiver preferably operates on a wireless protocol such as Bluetooth™, 802.15.4 or 802.11. The long-range wireless transmitter preferably transmits information over a terrestrial, satellite, or 802.11-based wireless network. Suitable networks include those operating at least one of the following protocols: CDMA, GSM, GPRS, Mobitex, DataTac, iDEN, and analogs and derivatives thereof.

The invention has many advantages. In particular, during day-to-day activities, a patient's ear undergoes significantly less motion than the patient's finger. This means a plethysmograph measured from the ear has a relatively high signal-to-noise ration and contains relatively few motion-related artifacts. When processed with the algorithm described herein, this results in an accurate, continuous measurement of blood pressure, heart rate, and pulse oximetry. Moreover, because the ear is closer to the heart than a finger, a pulse oximetry measurement made in this region is likely to correlate better with blood pressure. The optical ear module is comfortable, unobtrusive, and can easily be worn for a short (e.g. 24-hour period) without affecting the patient.

The cuff-less blood pressure-measuring device of the invention combines all the benefits of conventional cuff-based blood-pressure measuring devices without any of the obvious drawbacks (e.g., restrictive, uncomfortable cuffs). Its measurement is basically unobtrusive to the patient, and thus alleviates conditions, such as a poorly fitting cuff, that can erroneously affect a blood-pressure measurement.

The device is small and makes a non-invasive blood-pressure measurement in a matter of seconds. An on-board or remote processor can analyze the time-dependent measurements to generate statistics on a patient's blood pressure (e.g., average pressures, standard deviation, beat-to-beat pressure variations) that are not available with conventional devices that only measure systolic and diastolic blood pressure.

These same features mean the device can also be used in 'telemedicine' applications where measurements are made from a remote patient and wirelessly transmitted to a central, Internet-accessible computer. In this way patients with cardiac conditions can be characterized remotely over extended periods of time. This characterization, for example, can be made by a medical professional using a remote, Internet-accessible website.

With these advantageous features, medical professionals can characterize a patient's real-time blood pressure during their day-to-day activities, rather than rely on an isolated measurement during a medical check-up. This means, for example, a physician can delineate between patients exhibiting temporary increases in blood pressure during medical check-ups (sometimes called 'white coat syndrome') and patients who truly have high blood pressure. With the invention physicians can determine patients who exhibit high blood pressure throughout their day-to-day activities. In response, the physician can prescribe medication and then monitor how this affects the patient's blood pressure. In general, the current invention measures blood pressure in an accurate, real-time, comprehensive manner that is not possible with conventional blood pressure-monitoring devices.

These and other advantages of the invention will be apparent from the following detailed description and from the claims.

DETAILED DESCRIPTION OF THE INVENTION

Figures 1A, 1B:
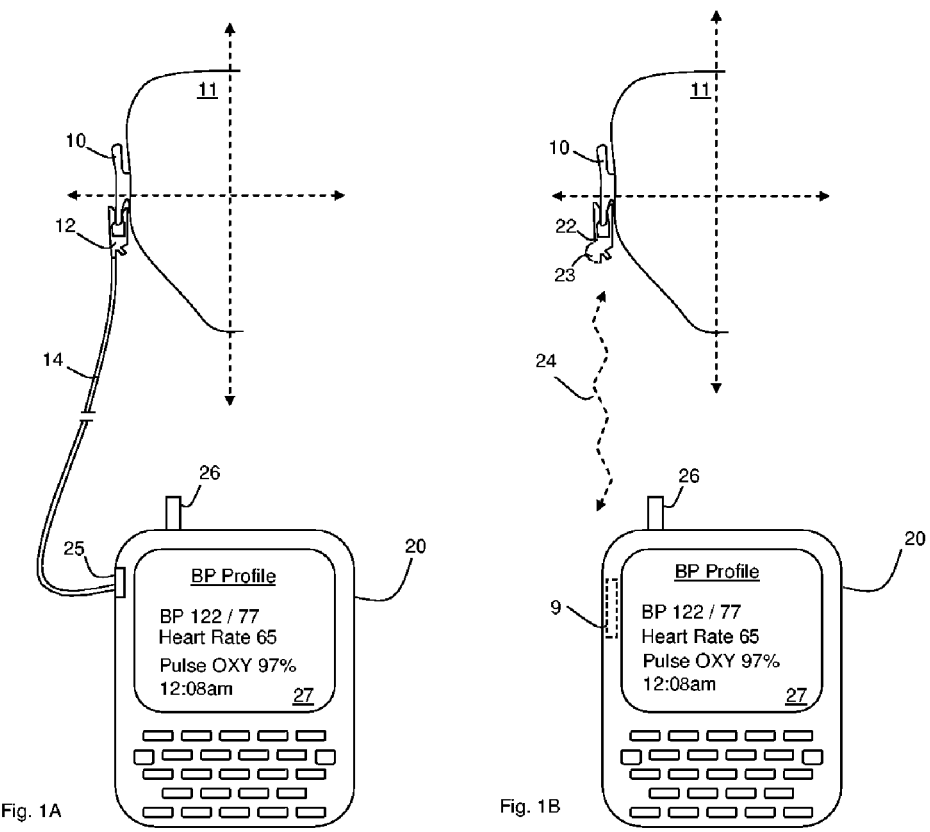
FIGS. 1A and 1B are a semi-schematic views of a system for measuring vital signs that includes an optical ear module and wireless hub connected by, respectively, a cable and a short-range wireless connection.

FIG. 1A shows an optical ear module 12 and wireless hub 20 for measuring vital-sign information (e.g., blood pressure, pulse oximetry, and heart rate) from an ear 10 of a patient 11. The optical ear module 12 clamps onto a lobe of the patient's ear 10 to make the measurement. An electric cable 14 connects the optical ear module to the wireless hub 20, which is typically worn around the patient's belt or arm like a portable radio. The optical ear module 12 features a pair of LEDs (described in detail with reference to FIG. 2) that generate, respectively, red and infrared radiation. A photodetector detects transmitted and scattered radiation and send this information to a microprocessor, which analyzes it as described in detail below to determine the vital signs.

The wireless hub 20, which can be a conventional cellular telephone or personal digital assistant, includes a serial port 25 that receives vital-sign information from the optical ear module 12 through the cable 14, and a display 27 that displays the information to the patient 11. The wireless hub 20 also includes an antenna 26 that wirelessly sends the vital-sign information through a wireless network to an Internet-accessible website as described with reference to FIG. 3.

FIG. 1B shows an alternate embodiment of the invention wherein an optical ear module 22 sends vital-sign information to the wireless hub 20 using a short-range wireless link 24. In this embodiment the optical ear module 22 includes a short-range wireless transmitter 23, and the wireless hub 20 features an embedded, matched short-range wireless transceiver 9. The optical ear module 22 attaches free from wires to the patient's ear 10 to increase mobility and flexibility. The short-range wireless transceiver 9 is preferably a transmitter operating on a wireless protocol, e.g. Bluetooth™, 802.15.4 or 802.11.

Figure 2:
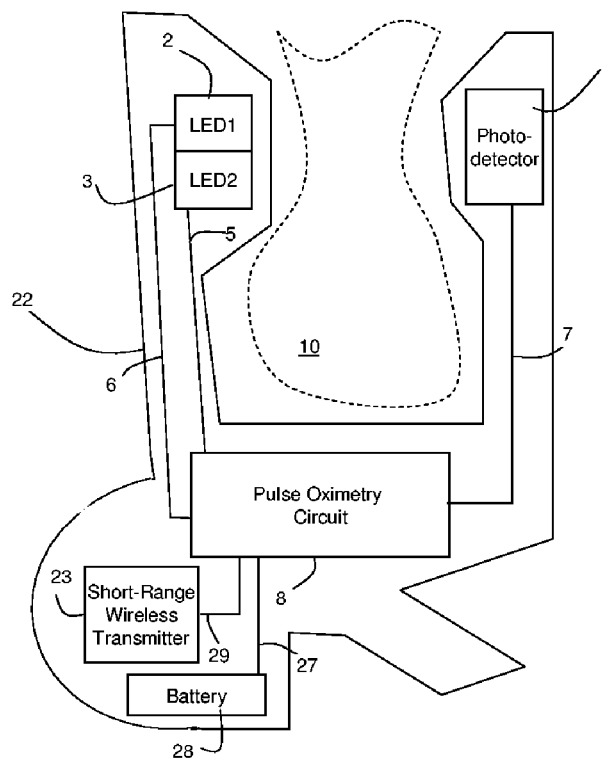
FIG. 2 is a semi-schematic top view of the optical ear module of FIG. 1B.

FIG. 2 shows in more detail of the optical ear module 22 of FIG. 1B. It includes red 2 and infrared 3 LEDs that emit radiation into the patient's earlobe 10. The module 22 also includes a photodetector 4 that detects scattered and transmitted radiation. The red 2 and infrared 3 LEDs and photodetector 4 connect, respectively, through electrical leads 5, 6, 7 to a pulse oximetry circuit 8. This circuit 8, in turn, connects through an electrical lead 29 to the short-range wireless transmitter 23. A battery 28 powers all the electrical components within the optical ear module.

To generate a plethysmograph and measure blood pressure, pulse oximetry, and heart rate, the red 2 and infrared 3 LEDs sequentially emit radiation that is partially absorbed by blood flowing through arteries within the earlobe 10. As the heart pumps, hemoglobin within the blood absorbs and transmits varying amounts of the red and infrared radiation depending on the amount of bound oxygen. The photodetector 4 detects a portion of radiation that is not absorbed, and in response generates a radiation-induced current for each wavelength. The current passes through the electrical lead 7 to the pulse oximetry circuit 8, which digitizes it to generate a corresponding plethysmograph. A firmware algorithm running on the pulse oximetry circuit 8 compares the relative absorption from the red 2 and infrared 3 LEDs to a look-up table to determine the patient's pulse oximetry.

A second firmware algorithm running on the pulse oximetry circuit 8 processes the plethysmograph to calculate blood pressure. One such algorithm for this calculation is described in U.S. patent application Ser. No. 10/967,610, filed Oct. 18, 2004, for a BLOOD PRESSURE MONITORING DEVICE FEATURING A CALIBRATION-BASED ANALYSIS, the contents of which are fully incorporated herein by reference. Specifically, this Patent Application describes how an optical module measures plethysmograph at the same time that a calibration is made using a conventional blood pressure-measuring device (e.g., a cuff-based device). The pulse oximetry circuit stores and analyzes the systolic and diastolic blood pressure values measured during the calibration measurement and the plethysmographs to complete the calibration.

In one embodiment, for example, the plethysmograph is 'fit' using a mathematical function that accurately describes its features and an algorithm (e.g., the Marquardt-Levenberg algorithm) that iteratively varies the parameters of the function until it best matches the time-dependent features of the plethysmograph. To accurately calculate blood pressure, the algorithm requires at least two calibration measurements, preferably made when the patient is in a different physiological state (e.g., has a different heart rate). Once this is complete, the firmware algorithm correlates the time-dependent features of the plethysmograph to blood pressure to generate a calibration table. The calibration device is then removed, and the optical ear module continuously measures plethysmographs from the patient's ear. The firmware algorithm analyzes each plethysmograph as described above to determine their time-dependent features, and compares these to the calibration table to determine blood pressure. The algorithm also determines pulse oximetry and heart rate as described above.

Additional methods for processing the optical waveform to determine blood pressure are described in the following co-pending patent applications, the entire contents of which are incorporated by reference: 1) U.S. patent application Ser. No. 10/810,237, filed Mar. 26, 2004, for a CUFFLESS BLOOD PRESSURE MONITOR AND ACCOMPANYING WEB SERVICES INTERFACE; 2) U.S. patent application Ser. No. 10/709,015, filed Apr. 7, 2004, for a CUFFLESS BLOOD-PRESSURE MONITOR AND ACCOMPANYING WIRELESS, INTERNET-BASED SYSTEM; and 3) U.S. patent application Ser. No. 10/752,198, filed Jan. 6, 2004, for a WIRELESS, INTERNET-BASED MEDICAL DIAGNOSTIC SYSTEM.

Figure 3:
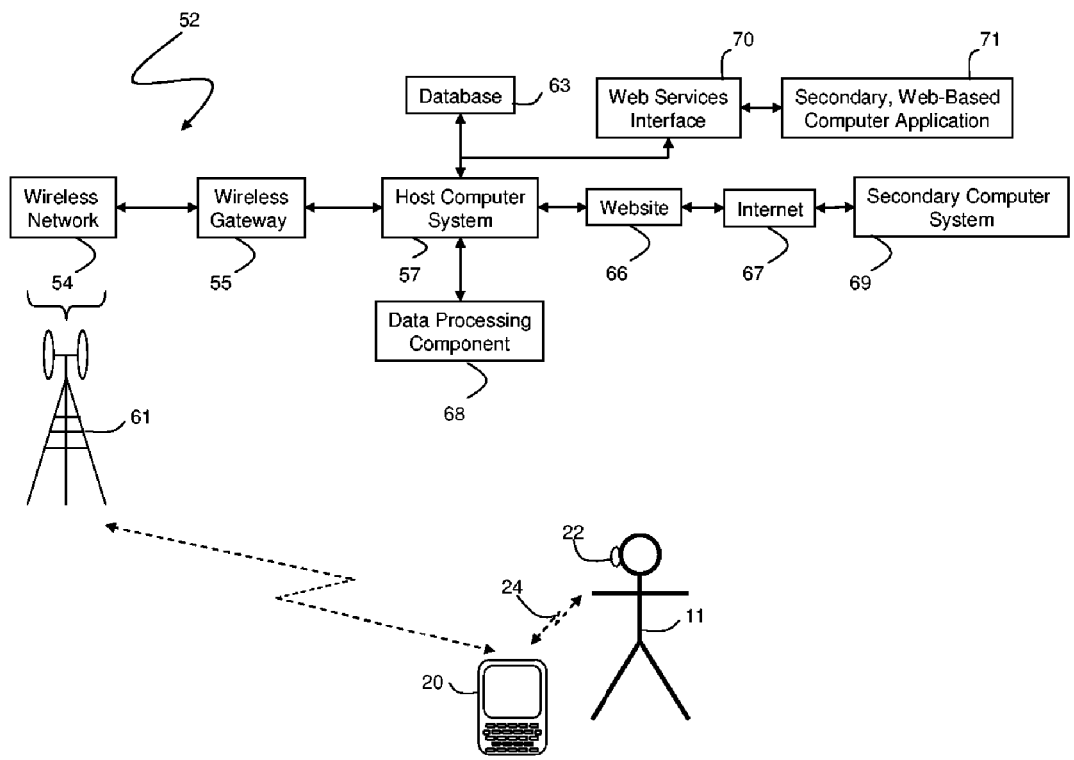
FIG. 3 is a schematic view of an Internet-based system, coupled with the system of FIG. 1, which transmits vital-sign information through a wireless network to an Internet-accessible computer system.

FIG. 3 shows a preferred embodiment of an Internet-based system 52 that operates in concert with the optical ear module system 10 and the wireless hub 20 to send information from a patient 11 through a wireless network 54 to a web site 66 hosted on an Internet-based host computer system 57. A secondary computer system 69 accesses the website 66 through the Internet 67. The system 52 functions in a bi-directional manner, i.e. the wireless hub 20 can both send and receive data. However most data flows from the wireless hub 20 using the same network.

A wireless gateway 55 connects to the wireless network 54 and receives data from one or more wireless hubs. The wireless gateway 55 additionally connects to a host computer system 57 that includes a database 63 and a data-processing component 68 for, respectively, storing and analyzing the data. The host computer system 57, for example, may include multiple computers, software pieces, and other signal-processing and switching equipment, such as routers and digital signal processors. The wireless gateway 55 preferably connects to the wireless network 54 using a TCP/IP-based connection, or with a dedicated, digital leased line (e.g., a frame-relay circuit, VPN or a digital line running an X.25 or other protocols). The host computer system 57 also hosts the web site 66 using conventional computer hardware (e.g. computer servers for both a database and the web site) and software (e.g., web server and database software).

During typical operation, the patient continuously wears the optical ear module 22 for a period of time, ranging from a 1-2 days to weeks. For longer-term monitoring (e.g. several months), the patient may wear the optical ear module 22 for shorter periods of time during the day. To view information sent from the wireless hub 20, the patient or medical professional accesses a user interface hosted on the web site 66 through the Internet 67 from the secondary computer system 69. The system 52 may also include a call center, typically staffed with medical professionals such as doctors, nurses, or nurse practioners, whom access a care-provider interface hosted on the same website 66.

Figures 4A, 4B:
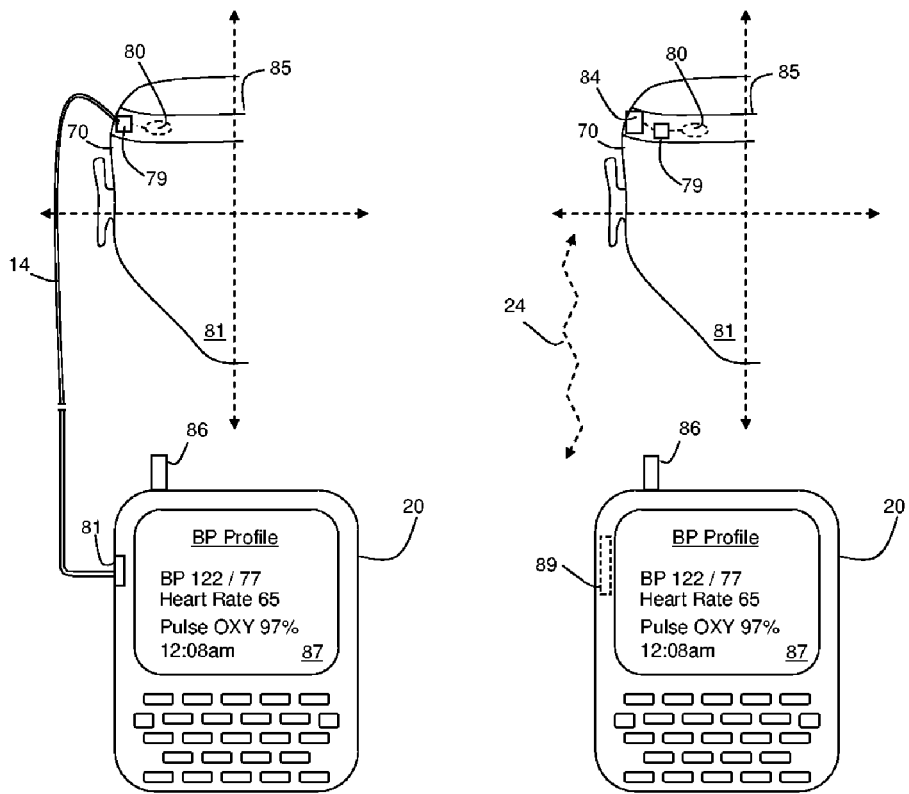
FIGS. 4A and 4B are semi-schematic views of an alternative system for measuring vital signs featuring a head-band with an optical system and a wireless hub connected, respectively, by a cable and short-range wireless connection.

FIG. 4A shows an alternate embodiment of the invention wherein a removable head-band 85 features an optical system 80 and a pulse oximetry circuit 79 that measures vital signs, e.g. pulse oximetry, heart rate, and blood pressure, as described above. The optical system 80 includes red and infrared LEDs and a photodetector similar to those described above that measure these properties from an artery within the forehead 70 of a patient 81. A cable 14 connects the pulse oximetry circuit 79 to a serial port 81 within a wireless hub 90. The wireless hub 90 includes a display 87 (e.g., an LCD or OLED display) that displays the vital signs, and an internal wireless transmitter that transmits the vital signs using an antenna 86 through a wireless network to the Internet. FIG. 4B shows another alternate embodiment of the invention where the removable head-band 85 additionally features a short-range wireless transmitter 84 that transmits vital signs from the pulse oximetry circuit 79 to a matched short-range receiver 9 the wireless hub 90.

Figure 5:
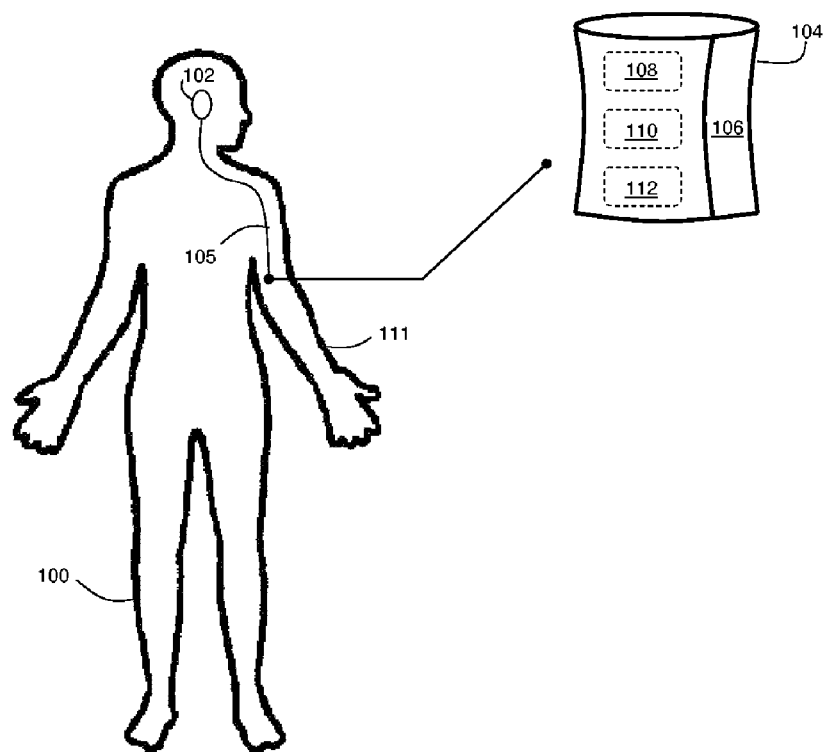
FIG. 5 is a semi-schematic view of the optical ear module of FIGS. 1A and 1B and a cuff-based calibration source.

FIG. 5 shows an alternate embodiment of the invention wherein a cuff 104 worn on the arm 111 of a patient 100 calibrates the optical ear module 102 to perform 'cuffless' measurements as described above, and also makes conventional cuff-based blood pressure measurements. The cuff 104 connects to the optical ear module 102 through a cable 105, and includes an internal bladder that inflates and deflates during a measurement, and a flexible covering 106 that houses electronics for processing information for both the cuff-based and cuffless measurements. The flexible covering 106 houses: i) a first circuit 108 that processes signals from the optical ear module 102 to determine blood pressure, pulse oximetry, and heart rate; ii) a second circuit 110 that controls the cuff-based measurement of blood pressure; and iii) a wireless transmitter 112 that receives information from the first 108 and second 110 circuits and sends it through a wireless network to an Internet-accessible website as described above with reference to FIG. 3. Typically in this embodiment the first circuit 108 includes a microprocessor that runs a firmware program that determines a cuffless blood pressure using information from the optical ear module 102 as described above. The firmware program additionally controls the second circuit 110, which includes a motor-controlled pump and data-collection electronics, to measure a cuff-based blood pressure.

During a typical operation, the patient 100 places the cuff 104 on their arm 111, and the microprocessor within the first circuit 108 initiates a calibration measurement. For the calibration measurement the first circuit 108 collects a plethysmograph from the optical ear module 102 through the cable 105 while simultaneously sending a command to the second circuit 110 to make a cuff-based measurement. This process is then repeated at a later time, preferably when the patient's heart rate is slightly elevated. To complete the calibration, the microprocessor 'fits' the plethysmograph to determine properties therein that vary with blood pressure. The microprocessor processes the properties along with the simultaneous cuff-based measurements to generate a calibration table that is used for subsequent measurements. Once the calibration table is determined, the first circuit makes periodic cuffless measurements and transmits this information with the wireless transmitter 112 to an Internet-accessible website. While a majority of the subsequent blood pressure measurements are cuffless, the microprocessor within the first circuit 108 may periodically command the second circuit 110 to make a cuff-based measurement. The wireless transmitter 112 can also send this information to the Internet-accessible website, along with a 'flag' that indicates it results from a cuff-based measurement.

Figure 6:
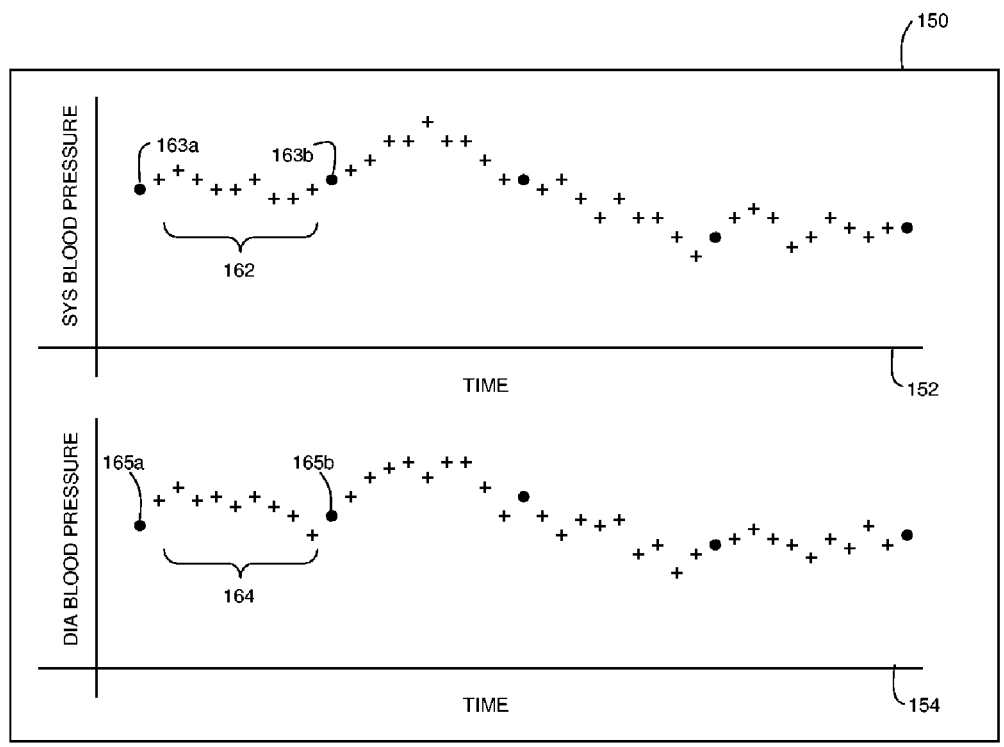
FIG. 6 is a schematic view of an Internet-accessible website that includes graphs that show both cuffless and cuff-based blood pressure measurements.

FIG. 6 shows graphs of a patient's systolic 152 and diastolic 154 blood pressures that can result, for example, using the system described with reference to FIG. 5. The graphs 152, 154, for example, can be displayed on a website 150 and include time-dependent curves that feature two types of data points: i) a first set of data points 163a,b 165a,b that indicate cuff-based blood pressure measurements; and ii) a second set of data points 162, 164 that indicate cuffless blood pressure measurements. The first set of data points 163a,b, 165a,b typically only represent a small percentage (e.g., about 10%) of the total blood pressure measurements. They are included in the graphs 152, 154 to verify to the viewer (e.g. the patient or a physician) that the cuffless measurements accurately indicate the patient's blood pressure.

Other embodiments are within the scope of the invention. For example, the placement of the above-described optical, mechanical, and electrical modules can be modified to change the form factor of the device. The device can also use algorithms other than those described above to process data. Or the device can consolidate various electronic components into a single silicon-based device. For example, the silicon-based device can include filters, memory, and an analog-to-digital converter.

In another embodiment, the optical module is designed to operate inside the inner ear canal. For example, the optical module may be embedded within a system that resembles an earplug from a pair of stereo headphones, or it may be included in a spongy foam material that expands to secure the system within the ear. This embodiment has the advantage that an optical module positioned within the ear suffers minimal motion-related artifacts and provides relatively artifact-free plethysmographs. Ultimately, when incorporated in the system according to the invention, this results in a relatively accurate blood pressure measurement, particularly during exercise or other periods of movement. This embodiment can include a wired or wireless attachment to a wrist or body-worn control module. Or it may include all necessary electronics within an ear-worn device. For example, the first circuit (108 in FIG. 5) and the wireless transmitter (112 in FIG. 5) may be included in a device that is worn around the ear, while the optical module is designed to fit within the ear. In this embodiment the device may also measure temperature using an optical method or a conventional thermocouple. The system may also include an acoustic component that broadcasts the patient's vital signs the inner ear so that the patient is made aware of their blood pressure, heart rate, temperature, and pulse oximetry.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

Still other embodiments are within the scope of the following claims.

What is claimed is:

1. A system for measuring blood pressure from a patient, comprising:
    an optical module comprising at least one optical source and a photodetector configured to measure a measurement signal;
    a processing module configured to receive the measurement signal and periodically determine a blood pressure according to a first pre-determined time period by fitting the measurement signal to a mathematical model and, in response, iteratively varying parameters of the mathematical model until it best matches the measurement signal, said processing module further configured to determine a blood pressure calibration signal according to a second pre-determined time period; and
    a wireless transmitter in electrical communication with the processing module and configured to periodically transmit the blood pressure to a host computer for display and the calibration signal to the host computer for display.

2. The system of claim 1, wherein the system further comprises an ear-worn clip that includes the optical module.

3. The system of claim 2, wherein the ear-worn clip comprises a first LED that emits red radiation, a second LED that emits infrared radiation, and the photodetector.

4. The system of claim 1, wherein the calibration source is a cuff-based blood pressure module that includes a cuff and a pump.

5. The system of claim 4, wherein the cuff is configured to be worn around the patient's arm.

6. The system of claim 1, wherein the wireless transmitter operates on a protocol based on 802.11, 802.15.4, part-15, or a derivative thereof.

7. The system of claim 1, further comprising a host computer comprising a wireless receiver configured to wirelessly receive the blood pressure and the blood pressure calibration signal from the processing module.

8. The system of claim 7, wherein the host computer is configured to cause the blood pressure and the blood pressure calibration signal to be displayed.

9. A system for monitoring a patient's blood pressure values, the system comprising:
    an optical module comprising at least one optical source, a photodetector and a transmitter for transmitting a measurement signal from the photodetector;
    a calibration source comprising a cuff-based blood pressure monitor, a first circuit for receiving the signal from the optical module, a second circuit for controlling the cuff-based blood pressure monitor and a wireless transmitter for periodically transmitting a cuffless-based signal from the first circuit and for periodically transmitting a cuff-based signal from the second circuit, the first circuit having a microprocessor programmed to control the second circuit and process the measurement signal from the optical module to periodically determine according to a first, pre-programmed time period a cuffless-based blood pressure value for the patient and to periodically determine according to a second pre-programmed time period a blood pressure calibration signal, the microprocessor programmed to determine the cuffless-based blood pressure value by fitting the measurement signal to a mathematical model and, in response, iteratively varying parameters of the mathematical model until it best matches the measurement signal; and
    a computer-based system for receiving the cuffless-based signal and the cuff-based signal from the wireless transmitter of the calibration source, the computer-based system comprising an interface configured to display the cuffless-based blood pressure values and cuff-based blood pressure values for the patient.

10. The system of claim 9 wherein the transmitter for the optical module is a short-range wireless transmitter that operates on a protocol based on 802.11, 802.15.4, part-15, or a derivative thereof.

11. The system of claim 9 wherein the transmitter for the optical module is a cable connected to the optical module and the calibration source.

12. The system according to claim 9 wherein the microprocessor of the first circuit of the calibration source comprises means for generating a calibration table from a cuff-based blood pressure value from the cuff-based blood pressure monitor and a plethysmograph generated from a signal from the optical module.

13. A system for measuring blood pressure from a patient, said system comprising:
- a cuff-based blood pressure monitor configured to periodically make a cuff-based blood pressure measurement according a pre-programmed first time period and generate a first signal representing the cuff-based blood pressure measurement comprising systolic and diastolic values;
- a cuffless blood pressure monitor comprising a light source configured to emit optical radiation, a light detector configured to receive the optical radiation after it is emitted from the light source and irradiates the patient's body, and a processor configured to receive a second signal from the light detector and the first signal from the cuff-based blood pressure monitor and process these with a mathematical algorithm to make a cuffless blood pressure measurement according to a pre-programmed second time period, the processor configured to determine a blood pressure by fitting the second signal to a mathematical model and, in response, iteratively varying parameters of the mathematical model until it best matches the second signal;
- a wireless transmitter in communication with the processor and configured to periodically receive and wirelessly transmit a first set of information, the first set of information describing a measurement from the cuff-based blood pressure monitor, and to periodically receive and wirelessly transmit a second set of information, the second set of information describing a measurement from the cuffless blood pressure monitor;
- a computer-based system configured to receive the wirelessly transmitted information describing cuff-based blood pressure measurements and the wirelessly transmitted information describing cuffless blood pressure measurements and to display the information describing both the cuffless and cuff-based blood pressure measurements in a time-dependent format.

14. The system of claim 13, wherein the computer-based system is configured to display a time-dependent plot of blood pressure that comprises the first set of information describing the measurements from the cuff-based blood pressure monitor, and the second set of information describing the measurement from the cuffless blood pressure monitor.

15. The system of claim 13, wherein the computer-based system is further configured to display a first portion that displays systolic blood pressure measurements, and a second portion that displays diastolic blood pressure measurements.

16. The system of claim 13, wherein the computer-based system in an Internet-based system.

17. The system of claim 13, wherein the wireless transmitter is comprised by a first module, and the processor is comprised by a second module.

18. The system of claim 17, wherein the wireless transmitter operates on a wireless network, and the first module further comprises a first short-range wireless transmitter.

19. The system of claim 18, wherein second module further comprises a second short range wireless transmitter that communicates with the first short-range wireless transmitter comprised by the first module.

20. The system of claim 19, wherein the second short-range wireless transmitter operates on a protocol based on 802.11, 802.15.4, part-15, or a derivative thereof.

21. The system of claim 18, wherein the wireless transmitter further comprises a transmitter operating on a CDMA, GSM, or 802.11-based network.

22. The system of claim 21, wherein the first short-range wireless transmitter operates on a protocol based on 02.11, 802.15.4, part-15, or a derivative thereof.

* * * * *